(12) United States Patent
Pan et al.

(10) Patent No.: US 10,814,004 B2
(45) Date of Patent: Oct. 27, 2020

(54) HYDROPHILIC POLYESTER AND A BLOCK COPOLYMER THEREOF

(71) Applicant: YINGU PHARMACEUTICAL CO., LTD., Tongzhou District, Beijing (CN)

(72) Inventors: Yuanyuan Pan, Beijing (CN); Shuqiang Zhao, Beijing (CN); Wenzhan Yu, Beijing (CN)

(73) Assignee: Yingu Pharmaceutical Co., Ltd., Beijing (CN)

( * ) Notice: Subject to any disclaimer, the term of this patent is extended or adjusted under 35 U.S.C. 154(b) by 153 days.

(21) Appl. No.: 16/067,270

(22) PCT Filed: Dec. 6, 2016

(86) PCT No.: PCT/CN2016/108636
§ 371 (c)(1),
(2) Date: Jun. 29, 2018

(87) PCT Pub. No.: WO2017/114102
PCT Pub. Date: Jul. 6, 2017

(65) Prior Publication Data
US 2019/0231879 A1 Aug. 1, 2019

(30) Foreign Application Priority Data
Dec. 31, 2015 (CN) .......................... 2015 1 1021362

(51) Int. Cl.
| | |
|---|---|
| *A61K 47/34* | (2017.01) |
| *C07D 309/30* | (2006.01) |
| *C08G 63/06* | (2006.01) |
| *C08G 63/688* | (2006.01) |
| *A61K 9/107* | (2006.01) |
| *C08G 63/78* | (2006.01) |
| *C08G 81/00* | (2006.01) |

(52) U.S. Cl.
CPC ............ *A61K 47/34* (2013.01); *A61K 9/1075* (2013.01); *C07D 309/30* (2013.01); *C08G 63/06* (2013.01); *C08G 63/688* (2013.01); *C08G 63/6882* (2013.01); *C08G 63/78* (2013.01); *C08G 81/00* (2013.01); *C08G 2230/00* (2013.01)

(58) Field of Classification Search
CPC .. C08G 63/06; C08G 63/688; C08G 63/6882; C08G 63/78; C08G 81/00; C08G 2230/00; A61K 47/34; A61K 9/1075; C07D 309/30
See application file for complete search history.

(56) References Cited

U.S. PATENT DOCUMENTS

| 4,532,169 A * | 7/1985 | Carley ................ B29C 53/8016 |
| | | 428/109 |
| 5,002,967 A | 3/1991 | Mueller et al. |
| 2002/0123476 A1 | 9/2002 | Emanuele et al. |

FOREIGN PATENT DOCUMENTS

| CN | 103288788 A | | 9/2013 |
|---|---|---|---|
| JP | 63-310821 A | | 12/1988 |
| JP | 07025955 A | * | 1/1995 |
| JP | 2006-509074 A | | 3/2006 |
| JP | 2009-029967 A | | 2/2009 |
| JP | 2012-501341 A | | 1/2012 |
| JP | 2014-524950 A | | 9/2014 |
| WO | WO 2004/050741 A1 | | 6/2004 |
| WO | WO 2010/025324 A2 | | 3/2010 |
| WO | WO 2013/004296 A1 | | 1/2013 |

OTHER PUBLICATIONS

International Search Report (ISR) for PCT/CN2016/108636; I.A. fd Dec. 6, 2016, dated Mar. 10, 2017, from the State Intellectual Property Office of the P.R. China, Beijing, China.
International Preliminary Report on Patentability (IPRP), Chapter I of the Patent Cooperation Treaty, including the Written Opinion for PCT/CN2016/108636; I.A. fd Dec. 6, 2016, dated Jul. 3, 2018, by the International Bureau of WIPO, Geneva, Switzerland.
Extended European search report, including the supplementary European search report and the European search opinion, for EP Appl. No. 16880892.1, dated Jul. 24, 2019, European Patent Office, Munich, Germany.
Xiwen Li et al., "Facile synthesis of well-defined hydrophilic polyesters as degradable poly(ethylene glycol)-like biomaterials," Polymer Chemistry, 2015, 6:6452-6456, DOI:10.1039/C5PY00762C, published Jul. 29, 2015, RSC Publishing.
Assala Al Samad, et al., "From nanospheres to micelles: simple control of PCL-g-PEG copolymers' amphiphilicity through thiol-yne photografting," Polymer Chemistry, 2015, 6:5093-5102, DOI: 10.1039/C5PY00391A, published Jun. 10, 2015, RSC Publishing.
Notice of Reasons for Rejection, for JP Application No. 2018-553284, dated Feb. 17, 2020, from the Japan Patent Office, Tokyo, Japan.
CN patent appl. No. 201511021362.X—Supplementary search dated Jul. 17, 2019, CNIPA (SIPO), Beijing, China.
CN patent appl. No. 201511021362.X—first office action, dated Jan. 9, 2019, CNIPA (SIPO), Beijing, China.

\* cited by examiner

*Primary Examiner* — Ali Soroush
(74) *Attorney, Agent, or Firm* — Sterne, Kessler, Goldstein & Fox P.L.L.C.

(57) ABSTRACT

The invention belongs to the field of macromolecules and biomedical materials, and relates to a polymer, a block copolymer comprising the polymer as a segment, methods for preparing the polymer and for preparing the block copolymer, a micelle particle or a vesicle particle prepared from the block copolymer, and a composition comprising the polymer, the block copolymer, the micelle particle and/or the vesicle particle. The polymer provided in the invention can be used as a novel biomedical material in in the fields such as pharmaceutical formulations, immunological formulations, and gene delivery reagents.

16 Claims, 10 Drawing Sheets

HYDROPHILIC POLYESTER AND A BLOCK COPOLYMER THEREOF

TECHNICAL FIELD

The invention belongs to the field of macromolecules and biomedical materials, and relates to a polymer, a block copolymer comprising the polymer as segment, methods for preparing the polymer and for preparing the block copolymer, a micelle particle or a vesicle particle prepared from the block copolymer, and a composition comprising the polymer, the block copolymer, the micelle particle and/or the vesicle particle. The polymer provided in the invention can be used as a novel biomedical material in the fields such as pharmaceutical formulations, immunological formulations, and gene delivery reagents.

BACKGROUND ART

Aliphatic polyester materials are a class of extremely valuable biomedical materials due to their good biocompatibility and biodegradability. However, aliphatic polyesters have poor hydrophilicity, which affects and limits their wider application in the field of biomedical materials.

In another aspect, polyethylene glycol (PEG) as an important medical supplementary material has been widely used in various fields of biomedicine due to its excellent hydrophilicity, high biocompatibility and biological inertness, as well as no immunogenicity. In particular, polyethylene glycol can effectively improve the in vivo circulation time and stability of a drug, can be used as an effective material for drug delivery, is widely used for the delivery of a protein, a polypeptide, DNA, RNA, and a small molecule drug, and plays a key role in the field of drug delivery.

However, with the wide application of PEG-based drug delivery systems, some potential drawbacks and shortcomings of PEG have also drawn more and more attention from the public gradually. Since polyethylene glycol has a polyether structure, one of its most important drawbacks is its inherent non-biodegradability. PEG with a lower polymerization degree can be excreted via renal route, while for PEG with a higher polymerization degree, the rate of clearance via renal route is reduced significantly, and it will be accumulated in human body.

Therefore, there is a demand for a biomedical material that cannot only have the biocompatibility and hydrophilicity of PEG, but also have the biodegradability of polyesters. Chinese patent ZL201310169131.8 discloses a method for preparing a polyester, comprising functionally modifying a δ-valerolactone compound by introducing a hydrophilic group, and carrying out controlled ring-opening polymerization of the compound, so as to obtain the polyester. Although the polyester prepared by this method has biodegradability as compared with polyethylene glycol, its hydrophilicity is not very satisfactory, and its solubility in water is only 10-20 mg/mL. Moreover, amphiphilic block copolymer prepared therefrom cannot form stable micelles or vesicles in a solution.

CONTENTS OF INVENTION

In the invention, unless otherwise specified, the scientific and technical terms used herein have the meanings as generally understood by a person skilled in the art. Moreover, the laboratory operations involved herein are the routine operations widely used in the corresponding fields.

In addition, in order to better understand the invention, the definitions and explanations of the relevant terms are provided as follows.

As used herein, the term "a micelle particle" refers to an assembly having a solid core-shell structure, which is formed by an amphiphilic molecule (e.g. an amphiphilic block copolymer) in a solvent (e.g. water) due to the interattraction of solvophobic moieties (e.g. hydrophobic moieties) or solvophilic moieties (e.g. hydrophilic moieties) when its concentration exceeds a certain critical value, wherein the core is formed by solvophobic moieties (e.g. hydrophobic moieties) of the molecule, and the shell is formed by solvophilic moieties (e.g. hydrophilic moieties) of the molecule. The concentration is the critical micelle concentration (CMC) of the molecule in the solvent. The micelle particles of an amphiphilic block copolymer can be formed by, for example, self-assembly in a solution.

As used herein, the term "a vesicle particle" refers to a closed and hollow assembly having a double-layered membrane structure, which is formed by an amphiphilic molecule (e.g. an amphiphilic block copolymer) in a solvent due to the interattraction of solvophobic moieties (e.g. hydrophobic moieties) or solvophilic moieties (e.g. hydrophilic moieties). The hollow portion of a vesicle may contain a solvent. The vesicle particles of an amphiphilic block copolymer can be formed by, for example, self-assembly in a solution.

As used herein, the term "particle size" refers to "an equivalent particle size", which means that when a certain physical property or physical behavior of a particle to be measured is most similar to that of a homogeneous sphere (or combination) with a certain diameter, the diameter of the sphere (or combination) is taken as the equivalent particle size (or particle size distribution) of the particle to be measured.

As used herein, the term "polypeptide" includes protein.

As used herein, the term "a small molecule compound" refers to a compound having a molecular weight of below 500.

As used herein, the term "a pharmaceutically acceptable supplementary material" refers to a substance other than an active ingredient, which is used in the production and making up of drugs, has been reasonably evaluated for safety, is comprised in a pharmaceutical formulation, and can have one or more of the functions such as acting as an excipient, serving as a carrier, enhancing stability, enhancing solubility, solubilization, and sustained-release, and controlled-release.

The inventor obtained a lactone monomer having a side group by conducting deep research and paying creative work, wherein a sulfone or sulfoxide group is used as a bridging unit for linking a side group to a lactone structure. The inventor surprisingly found that the lactone monomer had good hydrophilicity, thereby obtaining a hydrophilic polyester, and the polyester also had good biodegradability; an amphiphilic block copolymer could be synthesized from the polyester, and by adjusting the kinds and ratio of monomers, the hydrophilicity and hydrophobicity of the block copolymer could be modulated. Therefore, the following invention is provided.

In an aspect, the invention provides a polymer comprising repeat units of Formula (I);

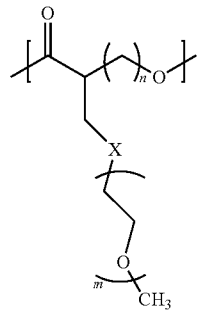

wherein, X is —SO— or —SO$_2$—;

m is 1-100, e.g. 1-10, 10-20, 20-30, 30-40, 40-50, 50-60, 60-70, 70-80, 80-90 or 90-100;

n is 1-10, e.g. 1-4, 2-5, 3-7, 4-6, 5-10, 6-8 or 7-10, e.g. 1, 2, 3, 4, 5, 6, 7, 8, 9 or 10.

In a preferred embodiment, m is 1-10, e.g. 1, 2, 3, 4, 5, 6, 7, 8, 9 or 10, more preferably, m is 3.

In a preferred embodiment, n is 2-5, e.g. 2, 3, 4 or 5, more preferably, n is 3.

In a preferred embodiment, m=3, and n=3.

In a preferred embodiment, the polymer is a homopolymer.

In a preferred embodiment, the polymer has a number-average molecular weight of 400-300000, e.g. 400-1000, 1000-5000, 5000-10000, 10000-50000, 50000-100000, 100000-200000 or 200000-300000.

In a preferred embodiment, the polymer has a structure of Formula (II):

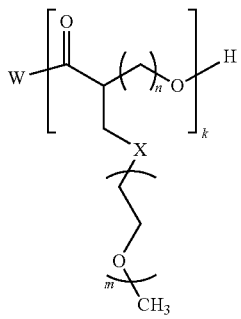

wherein, X, m and n have the same meanings as defined above;

k is 10-1000, e.g. 10-50, 10-100, 50-100, 100-200, 200-300, 300-400, 400-500, 500-600, 600-700, 700-800, 800-900 or 900-1000;

W is a terminal group, preferably, W is —OR, more preferably, —OR is a residual group of an initiator.

In a preferred embodiment, k is 10-100, e.g. 10-20, 20-30, 30-40, 40-50, 50-60, 60-70, 70-80, 80-90, 90-100, 10-50 or 50-100.

In a preferred embodiment, R is

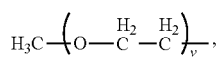

v=1-6, e.g. 1, 2, 3, 4, 5 or 6.

In a preferred embodiment, R has a general formula of:

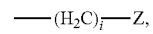

wherein i=0, 1, 2, 3 or 4, Z is selected from: —C≡CH,

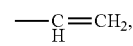

—NH$_2$, —N$_3$, —SH, —COOH, —CHO, —CH$_3$, —NHNH$_2$ and benzyl; more preferably, i=0, and Z is benzyl.

In a preferred embodiment, m=3, n=3, and k=10-100.

In a preferred embodiment, m=3, n=3, k=10-100, and R is benzyl.

In an aspect, the invention provides a method for preparing the polymer, comprising the step of carrying out a polymerization reaction using Compound 1 as a monomer; wherein Compound 1 has a structure of Formula (III);

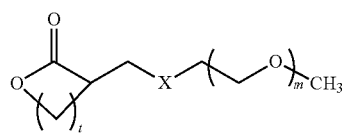

wherein, X and m have the same meanings as defined above.

t=1-10, e.g. 1-4, 2-5, 3-7, 4-6, 5-10, 6-8 or 7-10, e.g. 1, 2, 3, 4, 5, 6, 7, 8, 9 or 10.

In a preferred embodiment, the polymerization reaction is carried out in the presence of an initiator.

In a preferred embodiment, the initiator has a general formula of

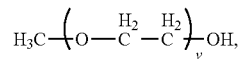

wherein, v=1-6, e.g. 1, 2, 3, 4, 5 or 6.

Preferably, the initiator is an alcohol compound; preferably, the alcohol compound is ROH, R has a general formula of:

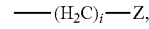

wherein i=0, 1, 2, 3 or 4, Z is selected from:

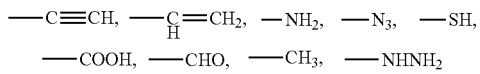

and benzyl; preferably, ROH is benzyl alcohol.

In a preferred embodiment, the polymerization reaction is carried out in the presence of a catalyst; preferably, the catalyst is selected from the group consisting of 1,5,7-triazabicylo[4.4.0]dec-5-ene (TBD), 1,8-diazabicyclo[5.4.0]undec-7-ene (DBU), diphenyl phosphate, 4-dimethylaminopyridine (DHAP), an organoaluminium compound, a tin compound, a rare earth compound, and any combination thereof; preferably, the catalyst is selected from the group consisting of diphenyl phosphate and 4-dimethylaminopyridine (DMAP).

In a preferred embodiment, the method comprises the following steps of:

(1) mixing Compound 1, the initiator and the catalyst at a molar ratio of 10-100:1:1-10, e.g. 10-50:1:1-10, 50-100:1:1-10, 10-100:1:1-5, 10-100:1:5-10, e.g. 10:1:1, 10:1:10, 100:1:1, 100:1:10, 50:1:1, 50:1:5;

preferably, the initiator is benzyl alcohol;

preferably, the catalyst is selected from the group consisting of diphenyl phosphate and 4-dimethylaminopyridine (DMAP);

(2) carrying out a polymerization reaction of the mixture obtained in the step (1) under a substantially water- and oxygen-free condition (e.g. under the protection of inert gas), at a reaction temperature of 15° C.-75° C., e.g. 15° C.-25° C., 25° C.-45° C., 45° C.-65° C., 25° C.-65° C. or 65-75° C., and for a reaction time of 0.5-240 h, e.g. 0.5-5 h, 5-10 h, 10-24 h, 24-48 h, 48-72 h, 72-120 h, 120-168 h or 168-240 h;

(3) optionally, adding a quencher (e.g. triethylamine) to quench the reaction, preferably, the amount of the quencher is 2-10 equivalents, e.g. 2-5, 5-8 or 8-10 equivalents of the catalyst; and (4) purifying the product; preferably, purifying the product by means of concentration, dialysis and/or freeze-drying.

In another aspect, the invention provides a block polymer, comprising a segment consisting of the repeat units of Formula (I).

In a preferred embodiment, the polymer is a diblock copolymer, for example, one segment of the block copolymer consists of the repeat units of Formula (I), and the other segment is a hydrophobic polymer segment, e.g. poly(L-lactide), polyglycolide or polycaprolactone, etc.

In a preferred embodiment, the block copolymer has a structure of Formula (IV):

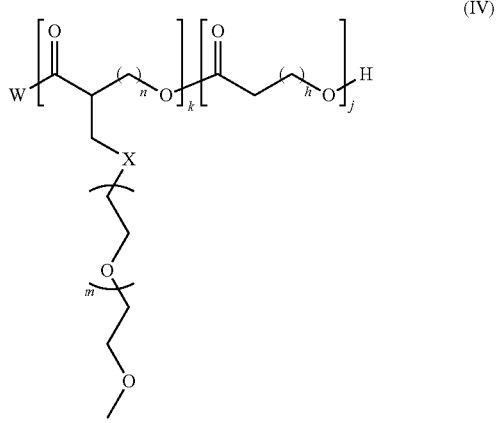

wherein, X, W, m, n and k have the same meanings as defined above;

h is 2-10, e.g. 2-5, 3-7, 4-6, 5-10, 6-8 or 7-10, e.g. 2, 3, 4, 5, 6, 7, 8, 9 or 10;

j is 10-1000, e.g. 10-50, 10-100, 50-100, 100-200, 200-300, 300-400, 400-500, 500-600, 600-700, 700-800, 800-900 or 900-1000.

In a preferred embodiment, h is 2-5, e.g. 2, 3, 4 or 5, more preferably, h is 4.

In a preferred embodiment, j is 10-100, e.g. 10-20, 20-30, 30-40, 40-50, 50-60, 60-70, 70-80, 80-90, 90-100, 10-50 or 50-100.

In a preferred embodiment, m=3, n=3, k=10-100, W is —OR, R is benzyl, and, h=4.

In a preferred embodiment, m=3, n=3, k=10-100, W is —OR, R is benzyl, h=4, and, j=10-100.

In another aspect, the invention provides a method for preparing the block copolymer, comprising the step of using a polymer having a structure of Formula (II) to initiate a polymerization reaction of a second monomer.

In a preferred embodiment, the second monomer is selected from lactones having 4-13 ring atoms, such as ε-caprolactone.

In a preferred embodiment, the polymerization reaction is carried out in the presence of a catalyst; preferably, the catalyst is selected from the group consisting of 1,5,7-triazabicylo[4.4.0]dec-5-ene (TBD), 1,8-diazabicyclo[5.4.0]undec-7-ene (DBU), diphenyl phosphate, 4-dimethylaminopyridine (DMAP), an organoaluminium compound, a tin compound, a rare earth compound, and any combination thereof; preferably, the catalyst is selected from the group consisting of diphenyl phosphate and 4-dimethylaminopyridine (DMAP).

In a preferred embodiment, the method comprises the following steps of:

(1) synthesizing a polymer having a structure of Formula (II), which is purified or not;

(2) adding a second monomer to carry out a polymerization reaction, preferably, the polymerization reaction is carried out under a substantially water- and oxygen-free condition (e.g. under the protection of inert gas);

(3) optionally, adding a quencher to quench the reaction; and (4) purifying the product, preferably, purifying the product by means of concentration, dialysis and/or freeze-drying.

In another aspect, the invention provides a micelle particle comprising the block copolymer as defined above.

In a preferred embodiment, the micelle particle has a particle size of 90-110 nm, e.g. 90 nm, 91 nm, 92 nm, 93 nm, 94 nm, 95 nm, 96 nm, 97 nm, 98 nm, 99 nm, 100 nm, 101 nm, 102 nm, 103 nm, 104 nm, 105 nm, 106 nm, 107 nm, 108 nm, 109 nm or 110 nm.

In a preferred embodiment, the micelle particle is loaded with a drug, such as a polypeptide, DNA, RNA and/or a small molecule compound.

In a preferred embodiment, the micelle particle is prepared by a method comprising the following steps of:

(1) dissolving the block copolymer in an organic solvent to obtain a solution;

(2) adding the solution obtained in the step (1) dropwise to water, so as to obtain a mixture; and (3) placing the mixture obtained in the step (2) in a dialysis bag, and carrying out dialysis in water.

In a preferred embodiment, in the step (1), the organic solvent is selected from the group consisting of dimethyl sulfoxide, tetrahydrofuran, ethanol, acetone and N,N-dimethylformamide.

In a preferred embodiment, in the step (1), the block copolymer and the organic solvent are used in a ratio of: block copolymer: organic solvent=5-10 mg: 1-5 mL.

In a preferred embodiment, the step (2) is carried out in an ice bath under ultrasonic condition.

In a preferred embodiment, in the step (3), the dialysis bag has a molecular weight cutoff of 1000-10000.

In a preferred embodiment, in the step (3), the dialysis is performed for 1-5 days.

In another aspect, the invention provides a vesicle particle, comprising the block copolymer as defined above.

In a preferred embodiment, the vesicle particle has a particle size of 150-250 nm, e.g. 150 nm, 160 nm, 170 nm, 180 nm, 190 nm, 200 nm, 210 nm, 220 nm, 230 nm, 240 nm or 250 nm.

In a preferred embodiment, the vesicle particle is loaded with a drug, such as a polypeptide, DNA, RNA and/or a small molecule compound.

In a preferred embodiment, the vesicle particle is prepared by a method comprising the following steps of:

(1) dissolving the block copolymer in an organic solvent to obtain a solution;

(2) injecting the solution obtained in the step (1) into water, and stirring until the organic solvent volatilizes completely; and (3) subjecting the product obtained in the step (2) to centrifugation, and then filtration.

In a preferred embodiment, in the step (1), the organic solvent is one selected from the group consisting of dimethyl sulfoxide, tetrahydrofuran, ethanol, acetone and N,N-dimethylformamide.

In a preferred embodiment, in the step (1), the block copolymer and the organic solvent are used at a ratio of: block copolymer: organic solvent=5-15 mg: 1-5 mL.

In a preferred embodiment, in the step (2), the water has a temperature of 25° C. -60° C.

In a preferred embodiment, in the step (2), the solution is injected to water at a speed of 0.1 mL/min-0.5 mL/min.

In a preferred embodiment, in the step (3), the speed of centrifugation is 1000-7000 rpm.

In a preferred embodiment, in the step (3), the centrifugation time is 1-40 min.

In a preferred embodiment, in the step (3), the filtration is performed for three times.

In a preferred embodiment, in the step (3), the three filtrations are carried out by using 0.8 μm, 0.45 μm and 0.22 μm microfiltration membrane in order.

In another aspect, the invention provides a pharmaceutical composition, comprising the polymer, the block copolymer, the micelle particle and/or the vesicle particle according to any of the aspects, and a drug (e.g. a pharmaceutically active ingredient).

In a preferred embodiment, the drug is selected from the group consisting of a polypeptide, DNA, RNA and a small molecule compound.

In a preferred embodiment, the pharmaceutical composition is present in a form of a formulation, for example, a pharmaceutical formulation or an immunological formulation.

In another aspect, the invention provides a composition comprising the polymer, the block copolymer, the micelle particle and/or the vesicle particle according to any of the aspects.

In a preferred embodiment, the composition is a pharmaceutically acceptable supplementary material.

In a preferred embodiment, the composition is a gene delivery reagent, such as a gene transfection reagent.

In a preferred embodiment, the composition is an immunoadjuvant.

In another aspect, the invention provides a compound having a structure of Formula (III):

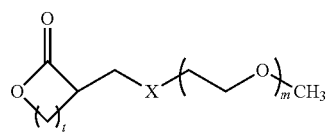

(III)

wherein, X is —SO— or —SO$_2$—;

m is 1-100, e.g. 1-10, 10-20, 20-30, 30-40, 40-50, 50-60, 60-70, 70-80, 80-90 or 90-100;

t=1-10, e.g. 1-4, 2-5, 3-7, 4-6, 5-10, 6-8 or 7-10, e.g. 1, 2, 3, 4, 5, 6, 7, 8, 9 or 10.

In a preferred embodiment, m is 1-10, e.g. 1, 2, 3, 4, 5, 6, 7, 8, 9 or 10, more preferably, m is 3.

In a preferred embodiment, t is 2-5, e.g. 2, 3, 4 or 5, more preferably, t is 3.

In an aspect, the invention provides a polymer, prepared by using a compound having a structure of Formula (III) as a monomer.

In a preferred embodiment, the polymer is a homopolymer, a random copolymer, a block copolymer, a graft copolymer or an alternating copolymer.

In a preferred embodiment, the polymer has a structure of Formula (I), Formula (II) or Formula (IV).

In an aspect, the invention provides a method for preparing a compound having a structure of Formula (III), comprising the step of carrying out an oxidization reaction of a compound of Formula (V);

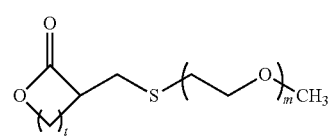

(V)

wherein, m and t have the same meanings as defined above.

In a preferred embodiment, the method comprises the step of carrying out an oxidization reaction using hydrogen peroxide or metachloroperbenzoic acid (mCPBA) as an oxidant.

In a preferred embodiment, the method comprises the step of carrying out an oxidization reaction using hydrogen peroxide as an oxidant; the compound obtained by the method has a structure of Formula (III), wherein, X is —SO—.

In a preferred embodiment, the method comprises the step of carrying out an oxidization reaction using metachloroperbenzoic acid (mCPBA) as an oxidant; the compound obtained by the method has a structure of Formula (III), wherein, X is —SO$_2$—.

Beneficial Effects of the Invention (1) The invention provides a novel degradable hydrophilic polyester prepared by controlled ring-opening polymerization using a functional lactone as a monomer, the hydrophilic polyester has excellent biocompatibility and biodegradability, and has improved hydrophilicity as compared with traditional aliphatic polyesters. The hydrophilicity of the hydrophilic polyester according to the invention is comparable to that of PEG with a similar molecular weight.

(2) The invention also provides an amphiphilic block copolymer comprising said polyester as a hydrophilic segment, and a method for preparing the same. In particular, said polyester is used as a hydrophilic segment, and a hydrophobic segment (such as poly(L-lactide), polyglycolide or polycaprolactone) is effectively introduced by controlled ring-opening polymerization, so as to prepare a degradable amphiphilic block copolymer.

(3) The amphiphilic block copolymer provided in the invention can be self-assembled into a micelle particle or a vesicle particle for delivering a polypeptide, DNA, RNA and/or a small molecule drug.

(4) The polymer provided in the invention can be used in the field of biomedicine, in the preparation of a pharmaceutical formulation, an immunological formulation or a gene delivery reagent, etc.

The embodiments of the invention are illustrated in detail by reference to the following drawings and examples. However, it is understood by those skilled in the art that the following drawings and examples are used only for the purpose of illustrating the invention, rather than limiting the protection scope of the invention. According to the detailed description of the following drawings and preferred embodiments, various purposes and advantages of the invention are obvious for those skilled in the art.

SPECIFIC MODES FOR CARRYING OUT THE INVENTION

The embodiments of the invention are illustrated in detail by reference to the following examples. However, it is understood by those skilled in the art that the examples are used only for the purpose of illustrating the invention, rather than limiting the protection scope of the invention. In the case where the concrete conditions are not indicated in the examples, the examples are carried out according to conventional conditions or the conditions recommended by the manufacturer. The agents or instruments of which the manufacturer are not indicated are regular products that can be purchased on the market.

EXAMPLE 1

Preparation of a Functional Lactone Monomer 1a

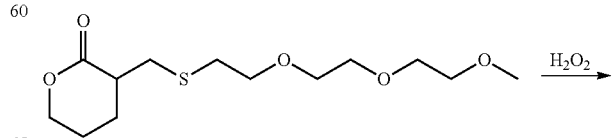

4

-continued

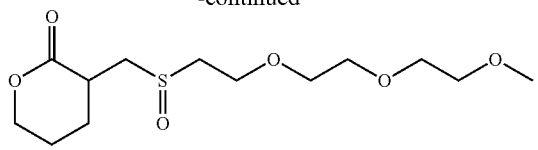

1a

Compound 4 was prepared by the method as described in CN patent ZL201310169131.8.

To a 25 mL round-bottom flask, 10 mL aqueous hydrogen peroxide solution (at a concentration of 30%) was added, and then Compound 4 (0.292 g, 1 mmol) was added. After stirring for 10 min, the water phase was extracted with 20 mL dichloromethane for three times, and the obtained organic phase was dried with anhydrous sodium sulfate. The drying agent was removed by filtration, and the solvent was removed by evaporation under reduced pressure, to obtain a functional lactone monomer 1a, as colorless oil (Yield: 84%).

$^1$H NMR (CDCl$_3$, 400 MHz) δ 4.25-4.17 (m, 2H), 2.85-2.77.91 (m, 3H), 3.41-3.871 (s, 8H), 3.35-3.18 (m, 7H), 2.54-2.49 (m, 1H), 1.99-1.93 (m, 2H), 1.85-1.71 (m, 1H). $^{13}$C NMR (100 MHz, CDCl3) δ 168, 70.69, 70.10, 70.11, 70.23, 67.36, 64.68, 58.83, 55.68, 55.10, 34.69, 24.97, 21.76. ESI MS calculated value: 308.4, measured value: [M+Na$^+$]=331.3.

EXAMPLE 2

Preparation of a Functional Lactone Monomer 1b

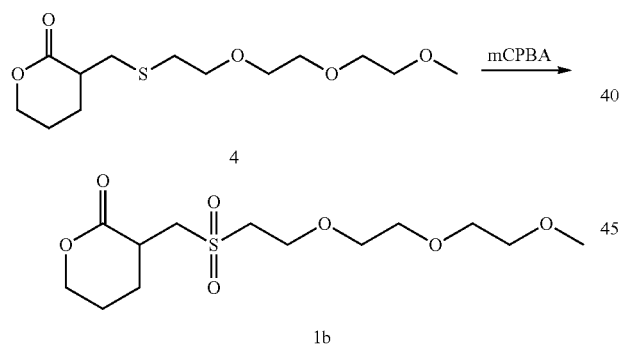

Compound 4 was dissolved in dichloromethane, and stirred in an ice-water bath, and then metachloroperbenzoic acid (mCPBA) was added slowly. After reacting at room temperature for 2 h, the resultant mixture was filtrated, and the filtrate was washed with a saturated sodium carbonate solution for more than three times. The organic phases were combined, and the solvent was removed by evaporation under reduced pressured, to obtain a functional monomer 1b, as light yellow oil (Yield: 87%).

$^1$H NMR (CDCl$_3$, 400 MHz) δ 4.39-4.36 (m, 2H), 3.94-3.91 (m, 3H), 3.65-3.51 (s, 8H), 3.35-3.18 (m, 7H), 2.54-2.49 (m, 1H), 1.99-1.93 (m, 2H), 1.85-1.71 (m, 1H). $^{13}$C NMR (100 MHz, CDCl3) δ 172, 71.76, 70.56, 70.31, 70.18, 68.41, 64.68, 58.83, 55.68, 55.10, 34.69, 24.97, 21.76. ESI MS calculated value: 324.1, measured value: [M+Na$^+$]= 347.3.

EXAMPLE 3

Synthesis of a Homopolymer of Monomer 1b

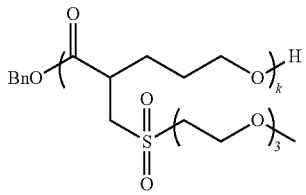

Figure 1:
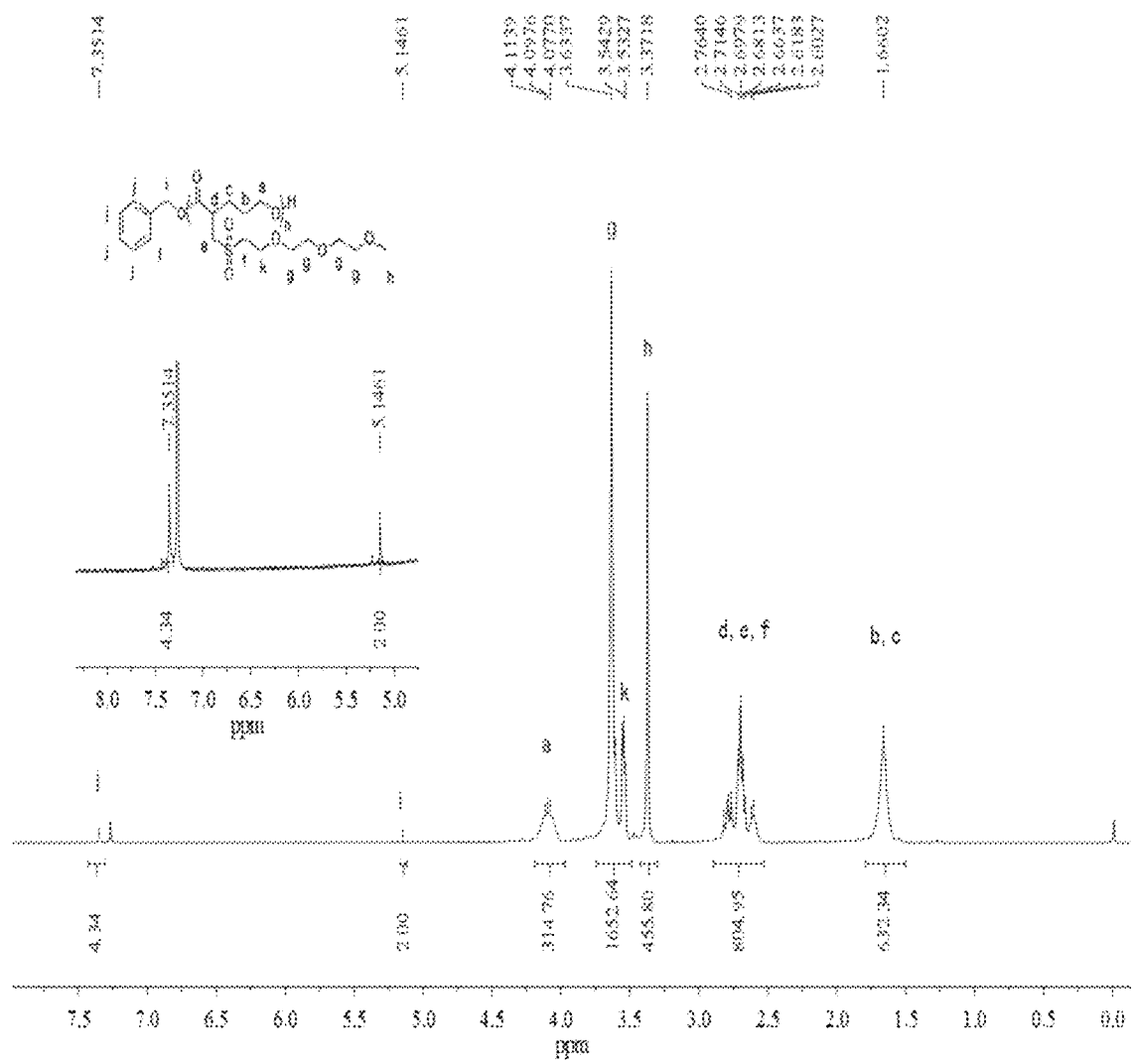
FIG. 1 is the $^1$H NMR spectrum of the homopolymer of the functional monomer 1b in Example 3 of the invention. The homopolymer has a polymerization degree of 100. In the figure, a-k represent the positions of hydrogen atoms, and in the structural formula, n represents a polymerization degree, which is different from the meaning of n in Formula (I), (II) and (IV).

In a glove box, substantially free of water and oxygen, under the protection of argon, to a 25 mL round-bottom flask, the monomer 1b (0.324 g, 1.0 mmol) and benzyl alcohol (1.1 mg, 0.01 mmol) were added, and after mixing homogeneously, 2.5 mg catalyst diphenyl phosphate (2.5 mg, 0.01 mmol) was added. After further stirring at room temperature for 24 h, 20 mL dichloromethane and triethylamine (0.3 g) were added, and the solvent was removed by rotary evaporation. The crude product was transferred to a dialysis bag (molecular weight cutoff of 1 kDa), and was dialyzed in a tetrahydrofuran solution (containing 40% water) for 1-7 d, during which the solvent was renewed twice. Finally, the dialysis solution was freeze-dried to obtain a polyester homopolymer (0.24 g), as yellowish oily liquid. As measured by Gel Permeation Chromatography (GPC), $M_n$=7325, $M_w$=7856, PDI=1.11, and polymerization degree k was 100. The $^1$H NMR spectrum of the product was shown in FIG. 1.

EXAMPLE 4

Synthesis of a Homopolymer of Monomer 1a

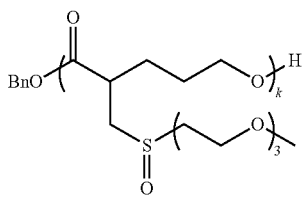

Figure 2:
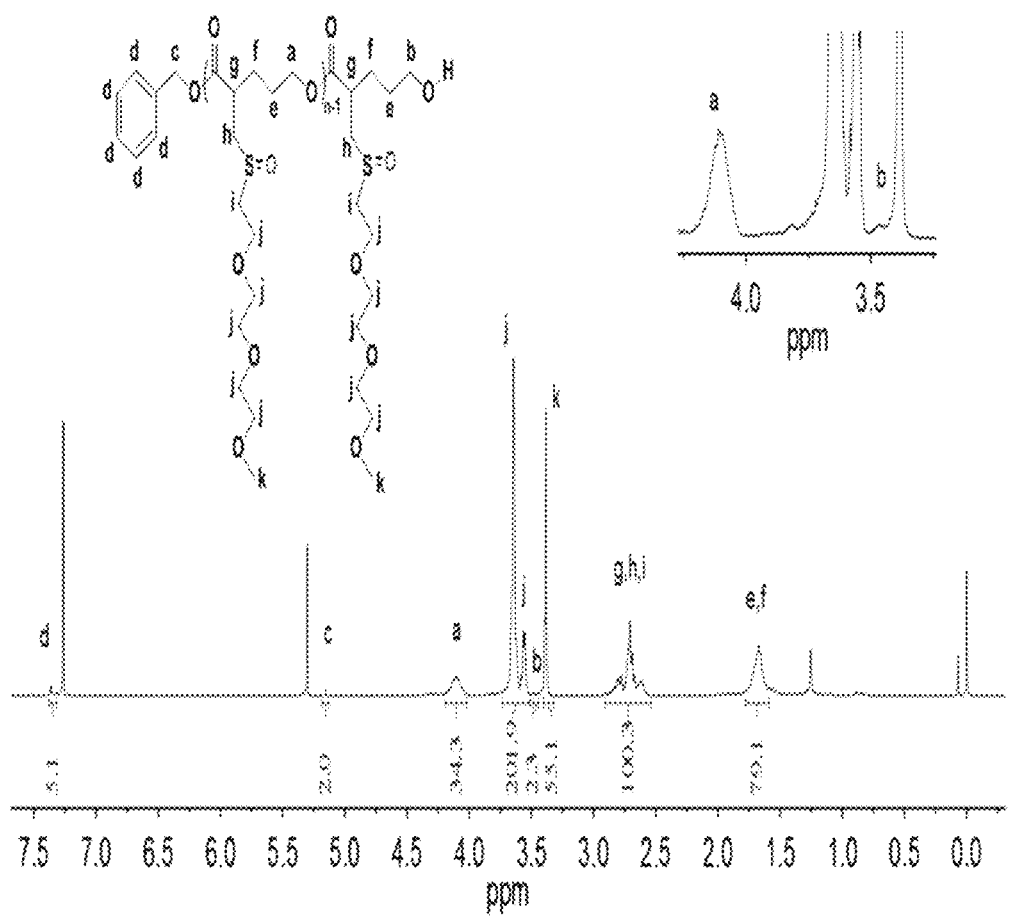
FIG. 2 is the $^1$H NMR spectrum of the homopolymer of the functional monomer 1a in Example 4 of the invention. The homopolymer has a polymerization degree of 10. In the figure, a-k represent the positions of hydrogen atoms, and in the structural formula, n represents a polymerization degree, which is different from the meaning of n in Formula (I), (II) and (IV).

In a glove box, substantially free of water and oxygen, under the protection of argon, to a 25 mL round-bottom flask, the monomer 1a (0.68 g, 0.45 mmol), benzyl alcohol (0.05 mmol), diphenyl phosphate (12.5 mg, 0.05 mmol) and 4-dimethylaminopyridine (DMAP) (6 mg, 0.05 mmol) were added, and stirred at 65° C. for 72 h. After cooling to room temperature, 10 mL dichloromethane and triethylamine (0.15 g) were added, and the solvent was removed by rotary evaporation. The crude product was transferred to a dialysis bag (molecular weight cutoff of 1 kDa), and dialyzed in a tetrahydrofuran solution (containing 20% water) for 1-7 d, during which the solvent was renewed twice. Finally, the dialysis solution was freeze-dried to obtain a polyester product (0.51 g), as light yellow oily liquid. As measured by Gel Permeation Chromatography (GPC), $M_n$=1106, $M_w$=1117, PDI=1.01, and polymerization degree k was 10. The $^1$H NMR spectrum of the product was shown in FIG. 2.

EXAMPLE 5

Synthesis of a Block Copolymer of Monomer 1b and ε-caprolactone

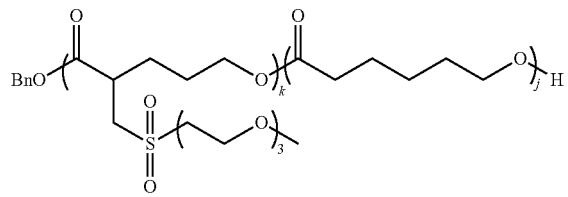

Figure 3:
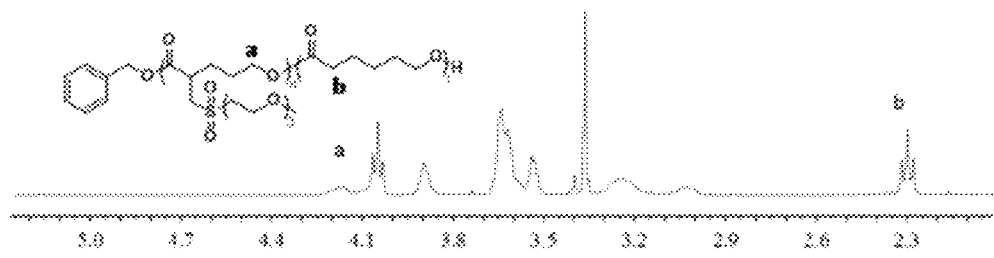
FIG. 3 is the $^1$H NMR spectrum of an amphiphilic diblock copolymer (P1b$_{50}$-b-PCL$_{50}$) in Example 5 of the invention. In the figure, a and b represent the positions of hydrogen atoms, and in the structural formula, n represents a polymerization degree, which is different from the meaning of n in Formula (I), (II) and (IV).
Figure 4:
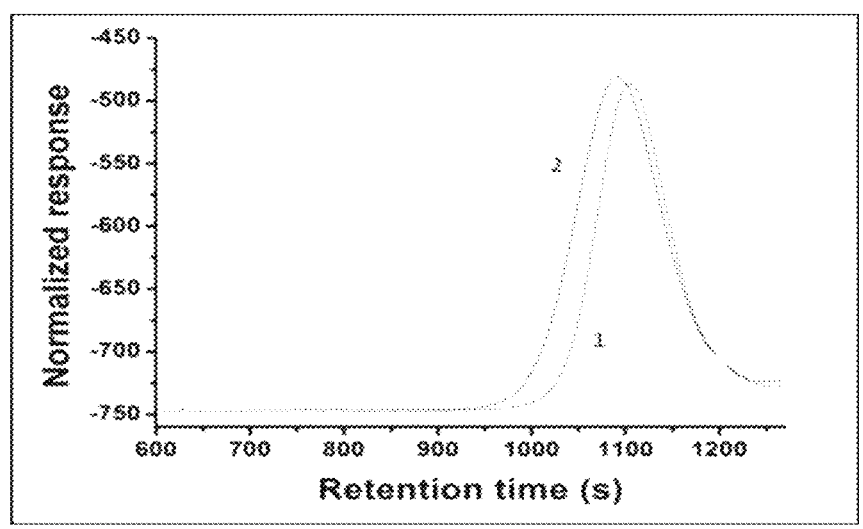
FIG. 4 shows the GPC curves of the hydrophilic segment P1b$_{50}$ (Curve 1) and its amphiphilic diblock copolymer (P1b$_{50}$-b-PCL$_{50}$) (Curve 2) in Example 5 of the invention. In the figure, the abscissa represents the elution time, and the ordinate represents the signal intensity of detector. As shown in the figure, P1b$_{50}$-b-PCL$_{50}$ had a shorter elution time than P1b$_{50}$, indicating an increase in molecular weight.

In a glove box, substantially free of water and oxygen, under the protection of argon, to a 25 mL round-bottom flask, the monomer 1b (0.324 g, 1 mmol) and benzyl alcohol (2.08 μL, 0.02 mmol) were added. Under stirring at room temperature, diphenyl phosphate (5 mg, 0.02 mmol) was added to the reaction flask. After further reaction for 48 h (the conversion percent of monomer 1b was greater than 95%), the hydrophilic segment P1b was obtained. 2 mL toluene and g-caprolactone (CL, 106.6 μL, 1 mmol) were added. After stirring for 12 h (the conversion percent of caprolactone was 100%), 15 mL dichloromethane and triethylamine (0.3 g) were added, and the solvent was removed by rotary evaporation. The crude product was transferred to a dialysis bag (molecular weight cutoff of 1 kDa), and was dialyzed in a tetrahydrofuran solution (containing 20% water) for 1-7 d, during which the solvent was renewed for three times. Finally, the dialysis solution was freeze-dried to obtain an amphiphilic diblock copolymer P1b-b-PCL, wherein, P1b was a hydrophilic segment, and PCL was a hydrophobic segment. P1b-b-PCL was a semitransparent white solid. As measured by Gel Permeation Chromatography (GPC), $M_n=7350$, $M_w=7791$, PDI=1.06. The $^1$HNMR spectrum of $P1b_{50}$-b-$PCL_{50}$ was shown in FIG. 3. It was determined by calculation that P1b had a polymerization degree of 50, and PCL had a polymerization degree of 50. The polymerization process as monitored by GPC was illustrated in FIG. 4. In the figure, Curve 1 was the GPC curve of the hydrophilic segment $P1b_{50}$, and Curve 2 was the GPC curve of the $P1b_{50}$-b-$PCL_{50}$. As shown in the figure, $P1b_{50}$-b-$PCL_{50}$ had a shorter elution time than $P1b_{50}$, indicating an increase in molecular weight.

EXPERIMENTAL EXAMPLE 1

Experiment on Hydrophilicity of Polymers

Figure 5:
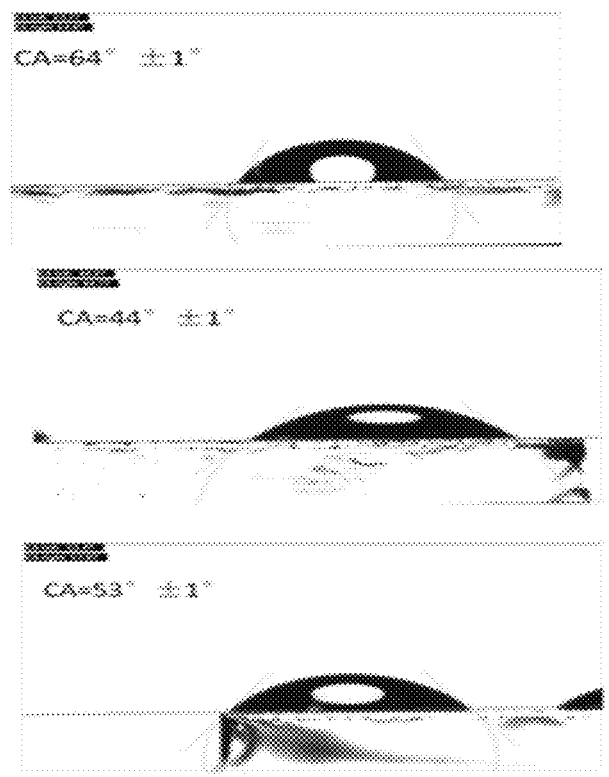
FIG. 5 is the experimental result of the water contact angle of a non-modified gold surface (upper figure, a water contact angle of 64±1°), an mPEG-SH (M$_n$ is 6500)-modified gold surface (middle figure, a water contact angle of 44±1°) and a hydrophilic polyester-modified gold surface (bottom figure, a water contact angle of) 53±1°) in Experimental example 1 of the invention. The result shows that the hydrophilicity of the gold surface modified by the hydrophilic polyester of the invention is comparable to that of the gold surface modified by PEG with a similar molecular weight.

According to the method described in Example 3, polymerization was carried out by using 1b as monomer and using an alcohol compound having a thiol functional group (OH—CH$_2$—CH$_2$—CH$_2$—CH$_2$—SH) as initiator, to obtain a polyester with a hydrophilic side chain ($M_n$=6880, PDI=1.11) wherein the terminal group was a thiol group. The polyester was linked to a gold surface, and a water contact angle assay was carried out. The result was shown in FIG. 5. The water contact angle of polyester-modified gold surface was very close that of mPEG-SH ($M_n$=6500)-modified gold surface. The experiment indicated that the polyester compound having a hydrophilic side chain was substantially comparable to PEG with a similar molecular weight in terms of hydrophilicity.

EXPERIMENTAL EXAMPLE 2

In Vitro Cytotoxic Assay of Polymers

The in vitro cytotoxicity of polymers was determined by MTT method, so as to verify the biocompatibility of polymers.

Human foreskin fibroblasts (HFF) growing well in logarithmic growth phase were used, and the medium was pipetted off and discarded. The residual medium was washed off with 1 mL 1×PBS, and PBS was pipetted off and discarded. A 2 mL 25% digestion solution (0.05% trypsin+ 0.02% EDTA) was added, and after digestion in an incubator for 4 min, when it was observed that the digestion solution turned yellow, the cells shrank and turned round, and most of the cells detached from the wall, the culture dish was shaken gently to have the cells almost completely detached from the wall, without blowing individual undetached cells. To the cell suspension, a 2 mL complete medium (DMEM high glucose medium+10% fetal bovine serum+1‰ Penicillin-Streptomycin) was added to stop digestion, and the culture dish could be shaken gently to mix the solution homogeneously. The cell suspension was transferred to a 15 mL centrifuge tube, and centrifuged at 900 rpm for 5 min. The supernatant solution was discarded. A 2 mL complete medium (DMEM high glucose medium+10% fetal bovine serum+1‰ Penicillin-Streptomycin) was added for washing, centrifugation was performed, and the supernatant solution was discarded. A 2 mL double antibodies-free medium (DMEM high glucose medium+10% fetal bovine serum) was added, and the cells were blew up gently, counted by a cell counting chamber, diluted to a desired density, and seeded to a 96-well plate. The 96-well plate was incubated in a 37° C., 5% CO$_2$ incubator for 24 h. The medium in each well was pipetted off, and a 100 μL aqueous solution of the polymer prepared in Example 3 was added to each well. The 96-well plate was incubated in a 37° C., 5% CO$_2$ incubator for 24 h. The sample solution in each well was pipetted off, and a 100 μL complete medium (DMEM high glucose medium+10% fetal bovine serum+1‰ Penicillin-Streptomycin) was added to each well, followed by the addition of a 20 μL MTT solution. The 96-well plate was incubated in a 37° C., 5% CO$_2$ incubator for 4 h. The sample solution in each well was pipetted off, and 150 μL dimethyl sulfoxide (DMSO) was added to each well to dissolve formazan crystal. The optical density value (OD value) at 490 nm for each well was measured by ELISA instrument. The plate wells containing no cells, to which DMSO was added, were used as blank control, and the OD value finally used in calculation should be the value obtained by subtracting the measured DMSO blank control value from the directly measured OD value of the experimental group. Cell viability was calculated in accordance with the following formula:

$$V = \frac{OD_{polymer} - OD_{DMSO}}{OD_{control} - OD_{DMSO}} \times 100\%$$

Figure 6:
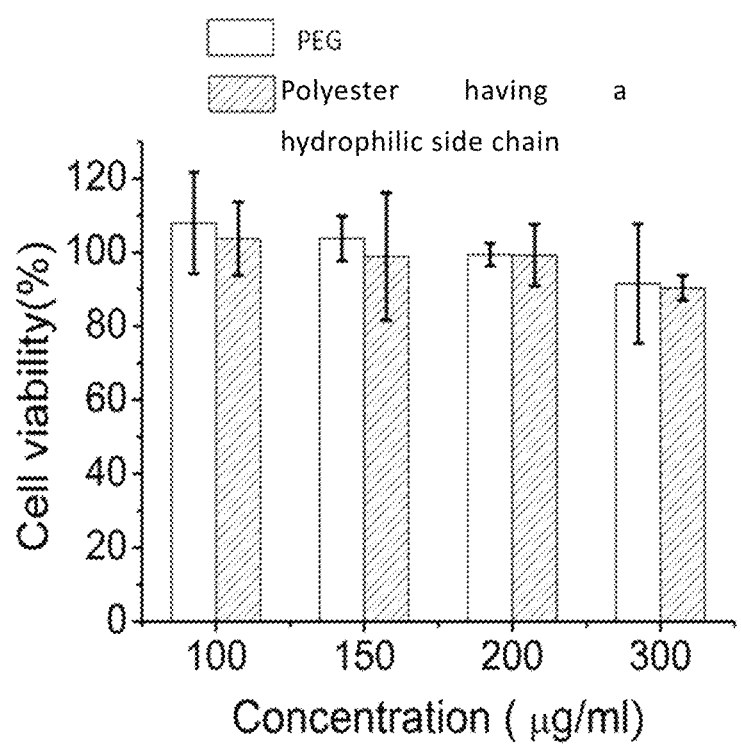
FIG. 6 is the experimental result of the in vitro cytotoxicity of polymers in Experimental example 2 of the invention. In the figure, the abscissa represents the concentration of polymer, and the ordinate represents cell viability. The result shows that the polymer of the invention had a cell viability comparable to that of PEG, i.e. had good biocompatibility.

The experimental result was shown in FIG. 6. In the figure, the abscissa represents the concentration of polymer, and the ordinate represents cell viability. The experimental result showed that the polyester having a hydrophilic side chain as disclosed in the invention was comparable to PEG in terms of cell viability, and had good biocompatibility as PEG did.

EXPERIMENTAL EXAMPLE 3

Cell Adhesion Inhibition Assay

Figure 7:
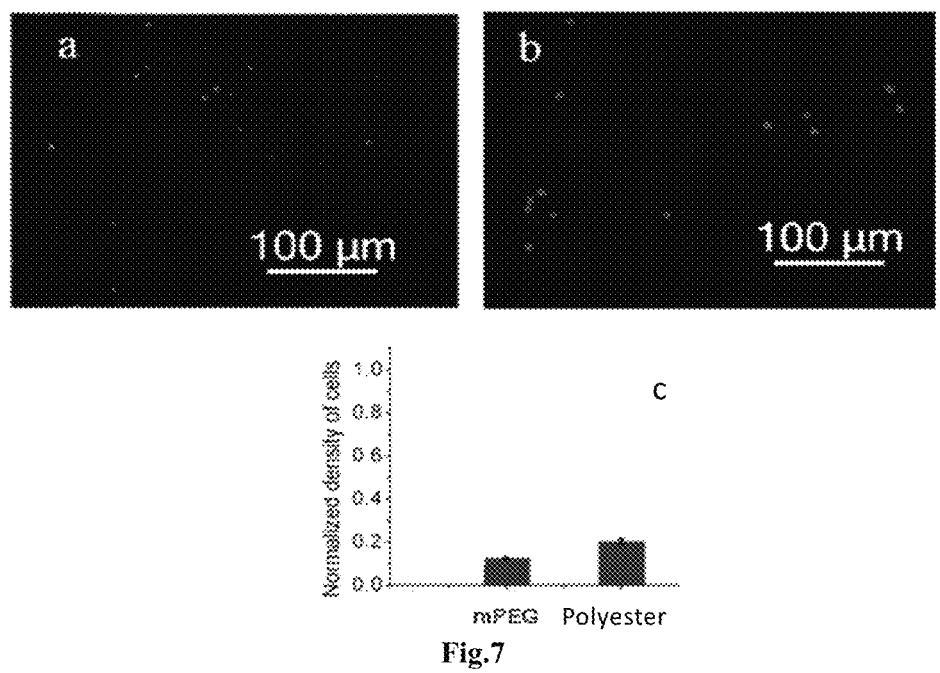
FIG. 7 is the experimental result of the in vitro inhibition of cell adhesion by polymers in Experimental example 3 of the invention. FIG. a is the fluorescent microscopic photograph of the gold surface modified by the polymer of the invention, and FIG. b is the fluorescent microscopic photograph of the gold surface modified by mPEG-SH. FIG. c shows the cell density on the gold surfaces modified by the polyester of the invention and mPEG-SH, respectively, wherein the cell density on both the two surfaces was very low. The experiment shows that the polyester material having a hydrophilic side chain according to the invention was comparable to PEG in terms of the property of cell adhesion inhibition.

Raw 264.7 cells were taken out from a culture bottle, digested, and floating in a medium. The cells were counted by a hemocytometer, and then the cells were diluted to $5 \times 10^5$ cells/mL. Gold-coated glass slides were modified by the polyester having a thiol group as terminal group as prepared in Experimental example 1, and mPEG-SH ($M_n$=6500), respectively. The modified gold-coated glass was divided into three identical parts, placed in sterile culture dishes, and soaked in 4 mL medium. 1 mL diluted cell suspension was added to each culture dish, so that the final density of cells was $1 \times 10^5$ cells/mL. The samples were incubated in an incubator (37° C., 5% $CO_2$) for 24 h, and the samples were rinsed with a medium to ensure that the unabsorbed cells were removed. The cells absorbed on the gold slides were stained with Calcein-AM. The viability of cells were then measured by fluorescent microscopic photography, and cell counting was also carried out under microscope. The experimental result was shown in FIG. 7, wherein FIG. a and FIG. b were the fluorescent microscopic photographs of the gold surface modified by the polyester of the invention and the gold surface modified by mPEG-SH, respectively. As shown in the figure, there were a very small number of cells on the gold surfaces modified by polyester and mPEG-SH ($M_n$=6500). FIG. c showed the cell density on the gold surfaces modified by the polyester of the invention and mPEG-SH, and the cell density on the two surfaces was very low. The assay showed that the polyester material having a hydrophilic side chain according to the invention was comparable to PEG with respect to the property of cell adhesion inhibition.

EXPERIMENTAL EXAMPLE 4

Polymer Degradation Experiment

Figure 8:
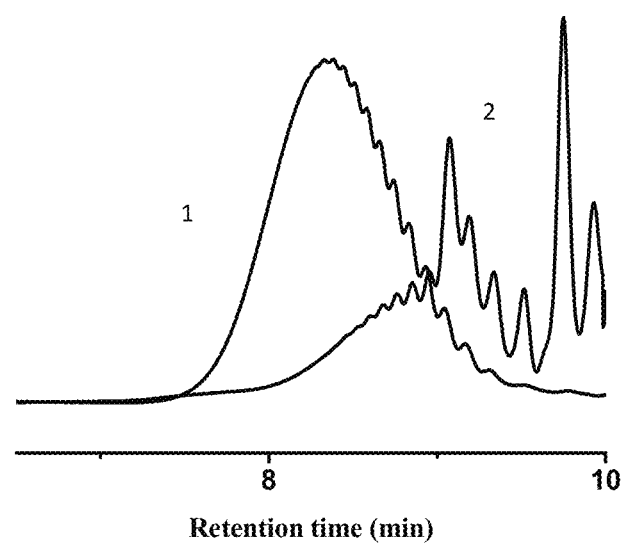
FIG. 8 is the GPC curves of polymer before degradation (Curve 1) and after degradation (Curve 2) in Experimental example 4 of the invention. As shown in the figure, after polymer degradation, the elution time of GPC increases, and the molecular weight of the polymer decreases. The result demonstrates that the polymer could be degraded under alkaline condition.

According to the method described in Example 3, polymerization was carried out by using 1b as monomer and using benzyl alcohol as initiator, so as to obtain a polyester ($M_w$=5423, 10 mg). The polyester was dissolved in methanol (5 mL), and a methanol solution of sodium methoxide (50 mg, 30 wt %) was added to the solution. The polyester was degraded under stirring at room temperature for 30 min, and the pH of solution was adjusted to a neutral pH by using a suitable concentration of HCl (2 M). The solvent was removed by rotary evaporation. The residue was dissolved in tetrahydrofuran (2 mL), and the resultant solution was analyzed by GPC. The result was compared with the GPC result before degradation. GPC curves were shown in FIG. 8. Curve 1 was the GPC curve before polyester degradation, and Curve 2 was the GPC curve after polyester degradation. As shown in the figure, after polymer degradation, the elution time of GPC increased, and the molecular weight of the polymer decreased. The experiment showed that the polyester material having a hydrophilic side chain according to the invention could be degraded under alkaline condition.

EXPERIMENTAL EXAMPLE 5

Figure 9:
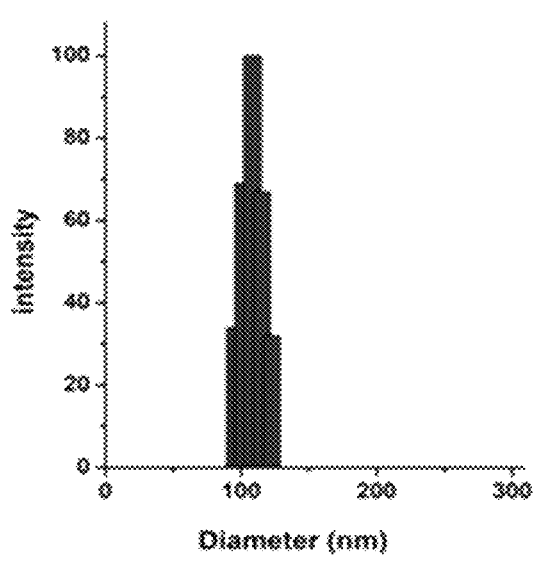
FIG. 9 shows the particle size distribution of the micelle particle of an amphiphilic diblock copolymer (P1b$_{50}$-b-PCL$_{100}$) as measured by a dynamic laser scattering apparatus in Experimental example 6 of the invention, wherein the micelle particle has a particle size of 90-110 nm.

According to the steps in Example 5, a block copolymer (P1b$_{50}$-b-PCL$_{400}$) of monomer 1b and ε-caprolactone was synthesized. 10 mg copolymer (P1b$_{50}$-b-PCL$_{100}$) was dissolved in 1 mL N,N-dimethylformamide, and the solution was added dropwise to 1 mL purified water in an ice bath under ultrasonic condition, and then the mixed solution was placed in a dialysis bag having a molecular weight cutoff of 1000, and dialyzed for 1 day, so as to obtain a micelle solution of the copolymer. The particle size of the micelle particle was measured, and the particle size distribution was shown in FIG. 9, wherein the particle size was 90-110 nm.

EXPERIMENTAL EXAMPLE 6

Figure 10:
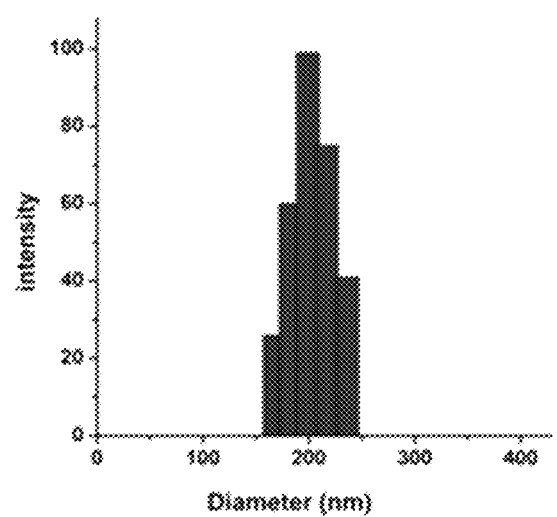
FIG. 10 shows the particle size distribution of the vesicle particle of an amphiphilic diblock copolymer (P1b$_{50}$-b-PCL$_{50}$) as measured by a dynamic laser scattering apparatus in Experimental example 7 of the invention, wherein the vesicle particle has a particle size of 150-250 nm.

According to the steps in Example 5, a block copolymer (P1b$_{50}$-b-PCL$_{50}$) of monomer 1b and ε-caprolactone was synthesized. 15 mg the copolymer (P1b$_{50}$-b-PCL$_{50}$) was dissolved in 1 mL N,N-dimethylformamide. The solution was injected to 30 mL purified water at a temperature of 25° C. at a speed of 0.1 mL per min, and was stirred until ethanol volatilized completely. A milk-white solution was obtained. The solution was centrifuged at 1000 rpm for 1 min, and filtrated through 0.8 μm, 0.45 μm, and 0.22 μm microfiltration membrane in order, so as to obtain a vesicle solution of the copolymer. The particle size of the vesicle particle was measured, and the particle size distribution was shown in FIG. 10, wherein the particle size was 150-250 nm.

Although the embodiments of the invention have been described in detail, a person skilled in the art would understand that according to all the disclosed teachings, details can be amended and modified, and these alterations all fall into the protection scope of the invention. The scope of the invention is defined by the attached claims and any equivalent thereof.

What is claimed is:

1. A polymer comprising repeat units of Formula (I);

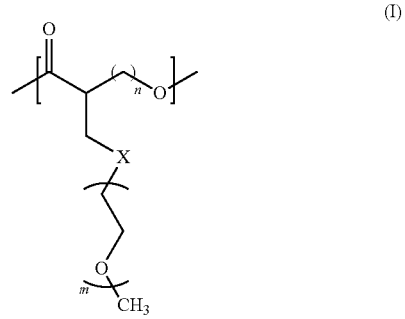

(I)

wherein, X is —SO— or —SO$_2$—;
m is 1-100; and
n is 1-10.

2. The polymer according to claim 1 having a structure of Formula (II):

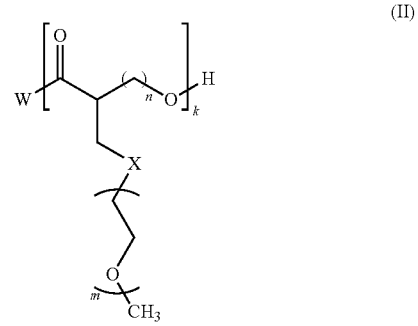

(II)

wherein, X, m and n have the same meanings as defined in claim 1;

k is 10-1000; and

W is a terminal group.

3. A method for preparing the polymer according to claim 1, comprising the step of carrying out a polymerization reaction using Compound 1 as a monomer; wherein, Compound 1 has a structure according to Formula (III);

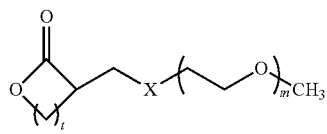

(III)

wherein, X and m have the same meanings as defined in claim 1; and t=1-10.

4. A block polymer, comprising a segment consisting of the repeat units of Formula (I).

5. A method for preparing the block copolymer according to claim 4, comprising the step of using a polymer having a structure of Formula (II) to initiate a polymerization reaction of a second monomer.

6. A micelle particle, comprising the block copolymer according to claim 4.

7. A vesicle particle, comprising the block copolymer according to claim 4.

8. A pharmaceutical composition, comprising the polymer according to claim 1, a block polymer comprising a segment consisting of the repeat units of Formula (I) in claim 1, a micelle particle comprising the block polymer and/or a vesicle particle comprising the block polymer, and a drug.

9. A composition, comprising the polymer according to claim 1, a block polymer comprising a segment consisting of the repeat units of Formula (I) in claim 1, a micelle particle comprising the block copolymer and/or a vesicle particle comprising the block copolymer.

10. The polymer according to claim 1, wherein the polymer has one or more features selected from:

(1) the polymer is a homopolymer;

(2) the polymer has a number-average molecular eight of 400-300000;

(3) m=3; and (4) n=3.

11. The block polymer according to claim 4, which is a diblock copolymer having a structure of Formula (IV):

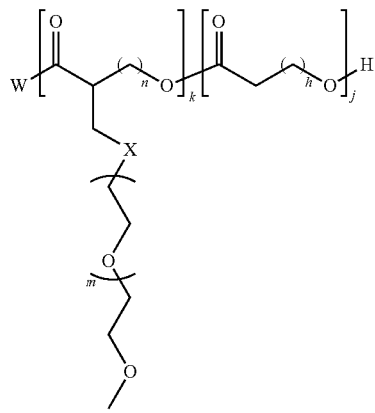

(IV)

Wherein X, W, m, n and k have the same meanings as defined in claim 2;

h is 2-10; and j is 10-1000.

12. The micelle particle according to claim 6, having one or more features selected from:

1) the micelle particle has a particle size of 90-110 nm;

2) the micelle particle is loaded with a drug;

3) the micelle particle is prepared by a method comprising the following steps of:

(1) dissolving the block copolymer in an organic solvent to obtain a solution;

(2) adding the solution obtained in the step (1) dropwise to water, so as to obtain a mixture; and (3) placing the mixture obtained in the step (2) in a dialysis bag, and carrying out dialysis in water.

13. The vesicle particle according to claim 7, having one or more features selected from:

1) the vesicle particle has a particle size of 150-250 nm;

2) the vesicle particle is loaded with a drug;

3) the vesicle particle is prepared by a method comprising the following steps:

(1) dissolving the block copolymer according to claim 4 in an organic solvent to obtain a solution;

(2) injecting the solution obtained in step (1) into water, and stirring until the organic solvent volatilizes completely; and (3) subjecting the product obtained in step (2) to centrifugation, and then filtration.

14. The pharmaceutical composition according to claim 8, wherein the drug is selected from the group consisting of a polypeptide, DNA, RNA and a small molecule compound.

15. The pharmaceutical composition according to claim 8, wherein the pharmaceutical composition is a pharmaceutical formulation or an immunological formulation.

16. The composition according to claim 9, which is a pharmaceutically acceptable supplementary material, a gene delivery reagent or an immunoadjuvant.

\* \* \* \* \*